(12) United States Patent
Zhang et al.

(10) Patent No.: US 6,831,184 B2
(45) Date of Patent: Dec. 14, 2004

(54) SKELETAL ISOMERIZATION OF FATTY ACIDS

(75) Inventors: Shuguang Zhang, New Rochelle, NY (US); Zongchao Zhang, Norwood, NJ (US); Dale Steichen, Göteborg (SE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/177,405

(22) Filed: Jun. 21, 2002

(65) Prior Publication Data

US 2003/0100780 A1 May 29, 2003

Related U.S. Application Data

(60) Provisional application No. 60/304,146, filed on Jul. 10, 2001.

(51) Int. Cl.[7] .............................................. C07C 51/00
(52) U.S. Cl. ...................... 554/158; 554/124; 554/141; 554/145; 502/77; 502/78
(58) Field of Search ................................ 554/125, 141, 554/145, 158; 502/78, 77

(56) References Cited

U.S. PATENT DOCUMENTS

| | | | |
|---|---|---|---|
| 2,812,342 A | 11/1957 | Peters | 260/409 |
| 3,395,100 A | 7/1968 | Fisher et al. | 252/8.8 |
| 3,865,855 A | 2/1975 | Linn et al. | 260/413 |
| 4,371,469 A | 2/1983 | Foglia et al. | 260/405.6 |
| 4,795,573 A | 1/1989 | Tsumadori et al. | 252/8.8 |
| 4,973,431 A | 11/1990 | Struve et al. | 260/409 |
| 5,364,949 A | 11/1994 | Neuss et al. | 554/161 |
| 5,401,865 A | 3/1995 | Laufenberg et al. | 554/141 |
| 5,481,025 A | 1/1996 | Laufenberg et al. | 554/142 |
| 5,677,473 A | 10/1997 | Tomifuji et al. | 554/158 |
| 5,856,539 A * | 1/1999 | Hodgson et al. | 554/125 |
| 6,455,716 B2 * | 9/2002 | Kenneally et al. | 554/158 |

FOREIGN PATENT DOCUMENTS

| | | | |
|---|---|---|---|
| EP | 0 306 237 | 3/1989 | ............ B01J/29/32 |
| EP | 0 683 150 | 11/1995 | ......... C07C/51/353 |
| EP | 0 774 451 B1 | 5/1997 | ......... C07C/51/353 |
| WO | 01/66507 | 9/2001 | ......... C07C/51/353 |

OTHER PUBLICATIONS

Van dew Waal et al; *Synthesis of All–silica Zeolite Beta.* J. Chem. Soc. Chem Commun., pp. 1241–1242 (1994).

W.C. Ault et al.; *Branched Chain Fatty Acids and Sulfonated Derivatives*; Journal of the American Oil Chemists' Society, vol. 42, Mar., 1965, pp. 233–236.

D.H. McMahon et al.; *Characterization of Products from Clay Catalyzed Polymerization of Tall Oil Fatty Acids*, Journal of the American Oil Chemists' Society, vol. 51, Dec., 1974, pp. 522–527.

D.V. Kinsman; *Isostearic and Other Branched Acids*; Journal of the American Oil Chemists' Society, vol. 56, Nov., 1979, pp. 823A–827A.

Y. Nakano et al.; *Thermal Alteration of Oleic Acid in the Presence of Clay Catalysts with Co–Catalysts*, Journal of the American Oil Chemists' Society, vol. 62, No. 5, May, 1985, pp. 888–891.

* cited by examiner

*Primary Examiner*—Deborah D. Carr
(74) *Attorney, Agent, or Firm*—Ralph J. Mancini

(57) ABSTRACT

The present invention relates to a process for the skeletal isomerization of unsaturated linear fatty acids to branched fatty acids which comprises contacting said unsaturated linear fatty acids with at least one large pore zeolite catalyst wherein said at least one zeolite catalyst comprises a material having a three dimensional channel structure having a pore diameter of at least 6.0 Å. In another embodiment, the invention relates to a process for the skeletal isomerization and hydrogenation of unsaturated linear fatty acids to saturated branched fatty acids which comprises contacting said unsaturated linear fatty acids with at least one metal-zeolite catalyst.

22 Claims, No Drawings

SKELETAL ISOMERIZATION OF FATTY ACIDS

This application claims benefit to U.S. Provisional Application No. 60/304,146, filed Jul. 10, 2001.

FIELD OF THE INVENTION

The present invention generally relates to a process for the isomerization of unsaturated fatty acids with a catalyst to branched fatty acids.

BACKGROUND OF THE INVENTION

Fatty acids are the building blocks for various compositions ranging from lubricants, polymers, solvents, cosmetics and the like. Fatty acids are generally obtained by hydrolysis of triglycerides of vegetable or animal origin. Naturally occurring triglycerides are esters of glycerol and generally straight chain, even numbered carboxylic acids, in size ranging from 10–24 carbon atoms. Most common are fatty acids having 12, 14, 16 or 18 carbon atoms. The fatty acids are either saturated or contain one or more unsaturated bonds.

Long, straight chain saturated fatty acids (C10:0 and higher) are solid at room temperature, which makes them difficult to process in a number of applications. Unsaturated long chain fatty acids, however, e.g. oleic acid are liquid at room temperature, so are easy to process, but are unstable because of the existence of double bond(s). Branched fatty acids mimic the properties of the straight chain unsaturated fatty acids in many respects, but do not have the disadvantage of being unstable. "Branched fatty acids" means fatty acids containing one or more alkyl side groups which are attached to the carbon chain backbone at any position. Therefore, branched fatty acids are for many applications more desirable than straight chain fatty acids. Commercial branched acids are not, however, naturally occurring materials.

Currently, branched fatty acids are obtained by isomerization (branching) of the straight chain, unsaturated fatty acids having a corresponding chain length. For example, branched C18:0 is prepared from straight C18:1 (or also C18:2). Various routes are known for said isomerization or branching of fatty acids in the art.

In one process, for example, clay is used as a catalyst. This clay catalyzed isomerization suffers from two main disadvantages. First, a considerable amount of undesired side products containing oligomers, saturated straight chain fatty acids and intermediate dimers is formed. A second disadvantage is that the clay catalyst cannot be reused.

U.S. Pat. No. 5,856,539 discloses an isomerization process whereby a fatty acid feed comprising unsaturated fatty acids is contacted with a catalyst, characterized in that the catalyst comprises a material having a microporous structure.

U.S. Pat. No. 5,677,473 describes a process for preparing branched chain fatty acids or alkyl esters thereof which comprises subjecting unsaturated fatty acids having 10–25 carbon atoms or alkyl esters thereof to a skeletal isomerization reaction in the presence of water or a lower alcohol using a zeolite as a catalyst. The zeolite has a linear pore structure of a size small enough to retard dimerization and large enough to allow diffusion of the branched fatty acids or alkyl esters thereof.

U.S. Pat. No. 5,364,949 describes a process for the production of branched fatty acids and their esters which comprises reacting unsaturated fatty acids or esters thereof with aliphatic nonactivated olefins in the presence of layer silicates and active carbon.

However, all of these processes are plagued by low yield and/or a high rate of undesireable byproduct formation. Accordingly, there is a need for a new process that overcomes these disadvantages, i.e. a process for the preparation of branched fatty acids from straight chain unsaturated fatty acid feedstocks with a high conversion rate, an increased selectivity towards branched monomeric isomers and which employs a reusable catalyst.

SUMMARY OF THE INVENTION

The present invention generally relates to a process for the skeletal isomerization of unsaturated linear fatty acids to branched fatty acids which comprises contacting said unsaturated linear fatty acids with at least one large pore acidic catalyst having a three dimensional channel structure. In another embodiment, the invention relates to a process for the skeletal isomerization and hydrogenation of unsaturated linear fatty acids to saturated branched fatty acids which comprises contacting said unsaturated linear fatty acids with at least one acidic catalyst loaded with at least one metal capable of hydrogenating unsaturated chemical bonds in the presence of hydrogen or a hydrogen source. The invention also relates to various softener compositions comprising actives prepared from the branched fatty acids of the present invention.

DETAILED DESCRIPTION OF THE PRESENT INVENTION

The present invention generally relates to a process for the skeletal isomerization of unsaturated linear fatty acids to branched fatty acids which comprises contacting said unsaturated linear fatty acids with at least one large pore acidic catalyst having a three dimensional channel structure. The present process advantageously converts fatty acid feedstock into a mixture that is rich in branched fatty acids and low in oligomers. While the reaction products of the present process will generally comprise both saturated as well as unsaturated branched fatty acids, both are thus included in the invention, there is high selectivity towards the formation of branched fatty acids. Optionally, the unsaturated branched fatty acids may be hydrogenated in any conventional way.

The acidic catalyst of this embodiment is characterized in that it comprises a material having a three dimensional pore structure wherein at least one of the channel structures has a pore size large enough to allow diffusion of the branched fatty acids and/or alkyl esters thereof. More particularly, at least one of the channel structures has a pore size large enough for the fatty acid to enter the pore and access the internal active sites. Typically, this pore size is at least about 5.5 Å, preferably at least 6.0 Å. Catalysts of this type having a three-dimensional channel structure have higher activity and are not as readily deactivated by pore mouth blockages compared to catalysts having one and/or two dimensional channel structures.

Various acidic catalysts having the required three dimensional pore structure and size are known to the skilled artisan. Examples of acidic catalysts employable in the claimed process include but are not limited to zeolites, acidic clays, molecular sieves and the like.

Zeolites are crystalline aluminosilicates generally represented by the formula $$M^{n+}{}_{p/n}[(AlO_2)p(SiO_2)_{q(q>p)}]mH_2O$$

where M is a metal cation of groups IA including Hydrogen or IIA and n is the valency of this metal. Zeolites consist of a network of $SiO_4$ and $AlO_4$ tetrahedra linked together via shared oxygen atoms.

As zeolite frameworks are typically negatively charged, the charge balancing cations related to this invention include monovalent cations such as $H^+$, $Li^+$ and the like, divalent cations such as $M^{2+}$, $Zn^{2+}$ and the like and trivalent cations such as $Ln^{3+}$, $Y^{3+}$, $Fe^{3+}$, $Cr^{3+}$ and the like. The framework composition of the three-dimensional zeolites may contain other elements in addition to Al and Si, such as, for example, P, Ti, Zr, Mn, and the like. Although any zeolite meeting the parameters of this embodiment of the present invention can be employed, faujasite (e.g. Y zeolite), Beta zeolite, Offeretite and the like are particularly well suited for the present process. The Si/Al ratio of the zeolites can vary depending on the particular zeolite employed provided that the skilled artisan understands that a ratio which is too low will result in more by-products and a ratio which is too high will lower the activity of the zeolite. In most cases the Si/Al ratio of the zeolites is at least 2, up to at least 20 and higher. For example, the Si/Al ratio for Beta zeolite may be from about 5–75 while that for Y zeolite can be from 2 to about 80.

Zeolites employable in the present process comprise a three-dimensional pore structure wherein at least one channel structure has a pore size large enough to allow diffusion of the branched fatty acids and/or alkyl esters thereof. In general, the larger the number of oxygen atoms in the ring opening, the larger the pore size of the zeolite. But this size is also determined by the structural shape of the ring. Zeolite materials having a three dimensional channel structure and a pore size of at least about 6.0 Å can generally be employed in the process of the invention. Such pore structures having a pore size of at least about 6.0 Å generally comprise 10 and/or 12 membered rings, or even larger rings in their structures.

It is known that zeolites having a three dimensional channel structure can be formed by zeolites having one dimensional channel with certain mineral acids such as nitric acid, hydrochloric acid and the like, and/or certain organo-carboxylic acids such as acetic acid and oxylic acid and the like. Other methods for generating zeolites with a three dimensional channel structure are known to the skilled artisan.

The subject process contemplates both both batch and fixed bed continuous processes which utilize the aforementioned zeolites.

Good selectivity and conversion can be obtained by the process of the present invention if at least part of the isomerization is performed at a temperature of between about 100° C. and 350° C. In another embodiment, the process of the invention is performed at a temperature of between about 230° C. and 285° C. Since the conversion is also a function of the reaction/contact time, it is preferred that the fatty acid feedstock is contacted with the catalyst for a period of at least 30 minutes and reaction times of 1–16 hours are typical. An even longer period could be used if the process is operated at a lower temperature.

In general, the amount of catalyst employed in the process according to the invention is between 0.5 and 20% by weight, based on the total reaction mixture. In another embodiment the amount of catalyst used between 2.5 and 10% by weight. In still another embodiment the catalyst amounts are between 3 and 7% by weight.

Additionally, it has been found that by using the catalyst system according to this invention it is possible to reuse the catalyst. In some cases it may be desired to add fresh catalyst while optionally removing a part of the spent catalyst, and in other cases regeneration of the catalyst may be desired. Regeneration can be effected by various methods know to the skilled artisan. For example, regeneration can be accomplished by utilizing controlled oxidative regeneration and/or by washing with a solvent.

Typical feedstocks comprise unsaturated linear alkylcarboxylic acids, related esters or mixtures thereof, optionally containing other organics. Since the present process is designed-for isomerization or conversion of unsaturated fatty acids into branched fatty acids, it is beneficial if the fatty acid feed comprises of at least about 30% by weight of unsaturated fatty acids. In another embodiment, the feedstock comprises at least 50% by weight of unsaturated fatty acids. Any unsaturated and/or polyunsaturated fatty acid, or mixtures thereof is suitable as a feedstock in accordance with the present invention. In one embodiment, the feedstock comprises oleic acid as the unsaturated fatty acid in an amount of at least 40% by weight. In an alternative embodiment, the feedstock comprises at least 70% by weight oleic acid.

Examples of zeolitic materials employable in the present embodiment include, but are not limited to zeolites having the following framework structures: CON, DFO, FAU, AFS, AFY, BEA, BPH, EMT, GME, MOR, and the like.

Other catalytic materials having a three dimensional pore structure can be employed in this embodiment of the invention provided that that they contain at least one channel structure having a pore size is large enough for the fatty acid to enter the pore and access the internal active sites. Examples of such materials include but are not limited to acidic clays and molecular sieves.

In another embodiment, the invention contemplates a process for the skeletal isomerization and hydrogenation of unsaturated linear fatty acids to saturated branched fatty acids in a single batch. This process comprises contacting said unsaturated linear fatty acids with at least one acidic support material loaded with at least one metal capable of hydrogenating unsaturated chemical bonds in the presence of hydrogen or a hydrogen source. In this embodiment, the acidic support material provides the acidic sites for the isomerization of unsaturated fatty acids and the metals allow for subsequent hydrogenation of the branched unsaturated fatty acids to saturated ones. A main advantage of this process is that the isomerization and the hydrogenation can be performed on a single catalyst and in a single batch.

In another embodiment, the skeletal isomerization and hydrogenation is conducted by a mixture of two or more catalysts, i.e., at least one acidic catalyst providing the requisite acidic sites for the isomerization of the unsaturated fatty acids and at least one catalyst loaded with at least one metal capable of hydrogenating the branched unsaturated fatty acids to saturated ones. In this embodiment, the isomerization and hydrogenation is performed in two steps in a single batch, i.e., for example, in a fixed bed reactor.

Examples of acidic support materials having utility in this embodiment of the invention include but are not limited to acidic zeolites and acidic clays and the like.

Zeolites usefully employed in this embodiment of the invention are typically acidic zeolites with or without metal ions, in addition to protons. Specific examples of zeolite structures include, but are not limited to faujasite, mordenite, USY, MFI, Mor, Y and Beta types.

Useful catalysts also include acidic clays with or without metal ions.

It is to be understood that if said acidic zeolites and/or said acidic clays are not loaded with metal ions, then a separate catalyst loaded with at least one metal capable of hydrogenating the branched unsaturated fatty acids may optionally be employed.

Whether a single catalyst is employed or whether two or more catalysts are employed, metal loading is typically below 20%.

Examples of suitable metals include, but are not limited to, Pt, Pd, Rh, Ir, Ru, Ni, Co, Cu and the like.

reactor under nitrogen. Under agitation, the reactor was heated to 250° C. within 30 minutes and maintained for 5 h. The reaction was terminated by cooling to room temperature within 20 minutes. The mixture was taken out of the reactor and the liquid product was separated from the solid catalyst by filtration. Reaction results were shown in Table 1.

TABLE 1

| | Time (h) | $\leq C_{10}$ | $i\text{-}C_{12}$ | $C_{12}$ | $i\text{-}C_{14}$ | $C_{14}^{1}$ | $C_{14}$ | $i\text{-}C_{16}$ | $C_{16}^{1}$ | $C_{16}$ | $i\text{-}C_{18}$ | $C_{18}^{1}$ | $C_{18}$ | lacton |
|---|---|---|---|---|---|---|---|---|---|---|---|---|---|---|
| Feed | — | 0.1 | 0.3 | 0.3 | 0.1 | 0.5 | 2 | 1.4 | 4.8 | 4.0 | 2.1 | 74.6 | 4.3 | 5.5 |
| Example 1 | 3 | 0 | 0.1 | 0.1 | 0.1 | 0 | 2.0 | 2.0 | 2.6 | 4.9 | 20.4 | 47.6 | 6.2 | 14.0 |
| Example 2 | 5 | 0.1 | 0.2 | 0.4 | 0.2 | 0 | 2.2 | 2.2 | 2.1 | 5.3 | 26.1 | 40.7 | 4.0 | 16.5 |
| Example 3 | 7 | 0.1 | 0.4 | 0.2 | 0.2 | 0 | 2.5 | 3.3 | 1.2 | 5.9 | 42.4 | 23.9 | 6.0 | 13.9 |
| Example 4 | 7 | 0.1 | 0.4 | 0.4 | 0.1 | 0 | 2.8 | 3.8 | 1.2 | 6.4 | 45.8 | 19.3 | 5.9 | 13.8 |
| Example 5 | 5 | 0.1 | 0.2 | 0.1 | 0 | 0 | 2.2 | 2.0 | 2.9 | 5.5 | 18.3 | 46.5 | 8.1 | 14.1 |

The invention will be illustrated by the following non-limiting examples.

EXAMPLE 1–3

These three examples show the conversion of oleic acid and the yield of branched fatty acid at different reaction periods on H-Beta zeolite catalysts. Experiments were carried out in a 135 ml autoclave reactor. For each reaction, two grams of H-Beta catalyst (Si/Al=25, pellets with 1 mm in diameter and 1–2 mm in length, precalcined in air at 550° C.) and 20 grams of oleic acid were loaded into the reactor under nitrogen. Under agitation, the reactor was heated to 250° C. within 30 minutes and maintained at this temperature for a specified time period (3 h in Example 1, 5 h in Example 2, and 7 h in Example 3, respectively). The reaction was terminated by cooling to room temperature within 20 minutes. The mixture was brought out of the reactor and the liquid product was separated from the solid catalyst by filtration. Compositions of feed and reaction products were shown in Table 1.

Results in Table 1 show that the conversion of oleic acid increased with the increase of reaction time. In the case of $C_{18}$ unsaturated fatty acid ($C_{18}^{1}$) in Example 3, the conversion is 68 wt % and the selectivity to its branched isomers is 79.5 wt %.

EXAMPLE 4

Two grams of H-Beta catalyst (Si/Al=50, powder, calcined in air at 550° C.) and 20 grams of oleic acid were loaded into the reactor under nitrogen. Under agitation, the reactor was heated to 250° C. within 30 minutes and maintained at this temperature for 7 h. The reaction was terminated by cooling to room temperature within 20 minutes. The mixture was taken out of the reactor and the liquid product was separated from the solid catalyst by filtration. Reaction results were shown in Table 1.

The conversion of $C_{18}^{1}$ fatty acid is 74.1 wt % and the isomerization selectivity is 79 wt %.

EXAMPLE 5

Two grams HY catalyst (Si/Al=80, powder, calcined in air 550° C.) and 20 grams of oleic acid were loaded into the

EXAMPLE 6

Two grams of H-Beta catalyst (Si/Al=50, powder, precalcined in air at 550° C.) and 20 grams of erucic acid were loaded into the reactor under nitrogen. Under agitation, the reactor was heated to 250° C. within 30 minutes and maintained for 7 h. The reaction was terminated by cooling to room temperature within 20 minutes. The mixture was taken out of the reactor and the product was separated from the solid catalyst by filtration with slightly heating. Compositions of erucic acid and reaction product were shown in Table 2.

These results indicated that erucic acid was highly branched.

EXAMPLE 7

Two grams H-Beta catalyst (Si/Al=25, pellets with 1 mm in diameter and 1–2 mm in length, precalcined in air at 550° C.) and 20 grams of erucic acid were loaded into the reactor under nitrogen. Under agitation, the reactor was heated to 280° C. within 30 minutes and maintained for 5 h. The reaction was terminated by cooling to room temperature within 20 minutes, the mixture was taken out of the reactor and the liquid product was separated from the solid catalyst by filtration. Compositions of erucic acid and reaction product were shown in Table 2.

TABLE 2

| | $C_{20}$ or less | $i\text{-}C_{22}$ | $C_{22}^{1}$ | $C_{22}$ | $i\text{-}C_{24}$ | $C_{24}$ | Other |
|---|---|---|---|---|---|---|---|
| Feed | 4.7 | 0.3 | 88.5 | 2.1 | 0 | 3.8 | 0.5 |
| Example 7 | 4.7 | 69.2 | 11.5 | 5.7 | 3.7 | 0 | 5.2 |
| Example 8 | 4.7 | 70.8 | 11.4 | 5.6 | 4.2 | 0 | 3.3 |

Example 7 showed that a similar isomerization result as that in Example 6 was achieved at a higher temperature but at a shorter reaction time.

EXAMPLE 8

Two grams of H-Beta catalyst (Si/Al=50, powder, precalcined in air at 550° C.) was loaded into a glass fixed bed reactor. A thermocouple in a thermowell was placed in the center of the catalyst bed. The catalyst was activated at 350° C. for 3 h in a 20 ml/min nitrogen flow. After activation, the reactor temperature was lowered to 250° C. and nitrogen flow rate was decreased to 1 ml/min. Oleic acid was pumped into the reactor at 2 ml/h. The results are shown in table 3, which indicate that a fixed bed process is also viable for the skeletal isomerization of unsaturated linear alkylcarboxylic acids.

EXAMPLE 10
Pt-HBeta, Isomerization Only

Ion exchange was carried out on a $NH_4^+$ Beta zeolite (Si/Al=50) using tetraammineplatinum nitrate solution. The exchanged catalyst was calcined in air at 550° C. before use. Two grams of this catalyst (Pt-HBeta) and 20 grams of oleic acid were loaded into the reactor under nitrogen. After sealed, the reactor was purged three times with ultra high purity nitrogen. A nitrogen pressure of 200 psig was

TABLE 3

| | Time (h) | $<=C_{10}$ | $i-C_{12}$ | $C_{12}$ | $i-C_{14}$ | $C_{14}^1$ | $C_{14}$ | $i-C_{16}$ | $C_{16}^1$ | $C_{16}$ | $i-C_{18}$ | $C_{18}^1$ | $C_{18}$ | lacton |
|---|---|---|---|---|---|---|---|---|---|---|---|---|---|---|
| Feed | — | 0.1 | 0.3 | 0.3 | 0.1 | 0.5 | 2 | 1.4 | 4.8 | 4.0 | 2.1 | 74.6 | 4.3 | 5.5 |
| Sample 1 | 2 | 0 | 0.9 | 0 | 0 | 0 | 3.0 | 6.3 | 2.0 | 8.7 | 38.9 | 21.8 | 6.0 | 12.4 |
| Sample 2 | 4 | 0 | 0.4 | 0 | 0 | 0 | 1.9 | 0.3 | 3.4 | 5.2 | 25.8 | 35.8 | 3.9 | 23.3 |
| Sample 3 | 6 | 0 | 0.2 | 0 | 0 | 0 | 1.8 | 1.6 | 2.6 | 4.9 | 19.4 | 47.9 | 3.5 | 18.1 |

EXAMPLE 9

Two grams of $Eu^{3+}$ exchanged Beta zeolite catalyst (Si/Al=50, powder, precalcined in air at 550° C.) and 20 grams of oleic acid were loaded into the reactor under nitrogen. Under agitation, the reactor was heated to 250° C. within 30 minutes and maintained for 7 h. The reaction was then terminated by cooling to room temperature within 20 minutes. The mixture was taken out of the reactor. The product was a liquid at room temperature and was separated from catalyst by filtration. GC analysis showed about 46% branched oleic acid yield from oleic acid ($C_{18}^1$).

COMPARATIVE EXAMPLE 1
Zeolite With One Dimensional Channel/pore Structure

Two grams Na-Mordenite catalyst (Zeolyst CP 500C-11, Si/Al=10, powder, precalcined in air at 550° C.) and 20 grams of oleic acid were loaded into the reactor under nitrogen. Under agitation, the reactor was heated to 250° C. within 30 minutes and maintained for 7 h. The reaction was then terminated by cooling to room temperature within 20 minutes. The mixture was taken out of the reactor and the liquid product was separated from the solid catalyst by filtration. GC analysis showed that there was less than 10 wt % branched oleic acid formed.

COMPARATIVE EXAMPLE 2

Two grams H-Mordenite catalyst (obtained by precalcination of $NH_4^+$ exchanged mordenite from Zeolyst CP 500C-11 at 550° C.) and 20 grams of oleic acid were loaded into the reactor under nitrogen. Under agitation, the reactor was heated to 250° C. within 30 minutes and maintained for 5 h. The reaction was then terminated by cooling to room temperature within 20 minutes. The mixture was taken out of the reactor. The product was solid at room temperature and it was separated from solid catalyst by melting and filtration. GC analysis showed that there was less than 10 wt % branched oleic acid formed.

approached at room temperature. With stirring at 1000 RPM, the mixture of oleic acid and catalyst was heated to 250° C. within 30 minutes and maintained for 7 h. After cooled down to room temperature within 20 minutes, the mixture was brought out of the reactor and the liquid product was obtained for analysis after separated from the solid catalyst by filtration. Compositions of feed and reaction products were shown in Table 4.

EXAMPLE 11
Pt-HBeta, Isomerization (250° C., 7 hr) Followed by Hydrogenation Two grams of Pt-HBeta catalyst and 20 grams of oleic acid were loaded into the reactor under nitrogen. After sealed, the reactor was purged three times with ultra high purity nitrogen. A nitrogen pressure of 200 psig was approached at room temperature. With stirring at 1000 RPM, the mixture of oleic acid and catalyst was heated up to 250° C. within 30 minutes and maintained for 7 h. The pressure was about 350 psig under these conditions. Hydrogen was added to reach a total pressure of 850 psig. Reaction was continued for another 2 h. After cooled down to room temperature within 20 minutes, the solid mixture was brought out of the reactor. The reaction product was obtained for analysis after separated from the solid catalyst by filtration with slightly heating. Product composition was shown in Table 4.

TABLE 4

| Example | $<=C_{10}$ | $i-C_{12}$ | $C_{12}$ | $i-C_{14}$ | $C_{14}^1$ | $C_{14}$ | $i-C_{16}$ | $C_{16}^1$ | $C_{16}$ | $i-C_{18}$ | $C_{18}^1$ | $C_{18}$ | lacton |
|---|---|---|---|---|---|---|---|---|---|---|---|---|---|
| feed | 0.09 | 0.26 | 0.32 | 0.11 | 0.46 | 2 | 1.37 | 4.83 | 4.01 | 2.07 | 74.57 | 4.29 | 5.62 |
| 1 | 0 | 0.39 | 0.11 | 0.36 | 0 | 2.79 | 3.01 | 1.05 | 6.6 | 43.03 | 18.94 | 4.14 | 19.58 |
| 2 | 0.04 | 0.6 | 0.1 | 0.89 | 0 | 2.46 | 4.71 | 0.31 | 7.44 | 49.21 | 1.86 | 27.59 | 4.79 |

EXAMPLE 12
Pt-HBeta, Isomerization (250° C., 15 h) Followed by Hydrogenation Three grams of Pt-HBeta catalyst and 30 grams of oleic acid were loaded into the reactor under nitrogen. After sealed, the reactor was purged three times with ultra high purity nitrogen. A nitrogen pressure of 50 psig was approached at room temperature. With stirring at 1000 RPM, the mixture of oleic acid and catalyst was heated up to 250°

C. within 30 minutes and maintained to the end of the run. The pressure was about 130 psig under these conditions. A sample (sample 1) was taken at 14 h. After 15 h, hydrogen was added to reach a total pressure of 600 psig. Reaction was continued for another 6 h. After cooled down to room temperature within 20 minutes, the mixture was brought out of the reactor. The reaction product (Sample 2) was obtained for analysis after separated from the solid catalyst by filtration. Product Composition was shown in Table 5.

TABLE 5

| Sample | <=$C_{10}$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | Lacton |
|---|---|---|---|---|---|---|---|---|---|---|---|---|---|
| 1 | 0.45 | 1.22 | 0 | 0.56 | 0 | 2.56 | 2.97 | 0.78 | 7.5 | 56.38 | 9.43 | 8.87 | 9.28 |
| 2 | 0.58 | 1.83 | 0 | 1.18 | 0 | 3.13 | 7.08 | 0.68 | 8.64 | 57.2 | 1.03 | 17.83 | 0.82 |

The conversions of $C_{18}$ unsaturated fatty acid in the three samples above and the selectivities to branched fatty acids were shown in Table 6. About 10 wt % of $C_{18}$ fatty acid was hydrocracked in sample 2.

TABLE 6

| Sample | $C_{18}^1$ conversion (wt %) | Isomerization selectivity (wt %) |
|---|---|---|
| 1 | 87.35 | 83.37 (Unsaturated) |
| 2 | 98.62 | 74.97 (Saturated) |

EXAMPLE 13

Pt-HBeta, Isomerization (280° C., 5 h) Followed by Hydrogenation

Two grams of Pt-HBeta catalyst and 20 grams of oleic acid were loaded into the reactor under nitrogen. After sealed, the reactor was purged three times with ultra high purity nitrogen. A nitrogen pressure of 50 psig was approached at room temperature. With stirring at 1000 RPM, the mixture of oleic acid and catalyst was heated up to 280° C. within 30 minutes and maintained for 5 h. After cooled down to 200° C., the nitrogen was replaced with 500 psig hydrogen and reaction was continued for another 4 h. The mixture was brought out of the reactor and the liquid product was obtained for analysis after separated from the solid catalyst by filtration. Composition of the reaction product was shown in Table 7.

Ion exchange was carried out on $NH_4^+$ Beta zeolite (Si/Al=50) using tetraamminepalladium nitrate solution. The exchanged catalyst was calcined in air at 550° C. and reduced with hydrogen (20 ml/min) in a fixed bed reactor at 250° C. for 2 h before use. Two grams of reduced Pd-HBeta catalyst and 20 grams of oleic acid were loaded into the reactor under nitrogen. After sealed, the reactor was purged three times with ultra high purity nitrogen. A nitrogen pressure of 50 psig was approached at room temperature after a leak test at 600 psig $N_2$ showed a good sealing. With stirring at 1000 RPM, the mixture of oleic acid and catalyst was heated up to 280° C. within 30 minutes and maintained for 5 h. After cooled down to 200° C., the nitrogen was replaced with 550 psig hydrogen and reaction was continued for another 4 h. The mixture was brought out of the reactor and the product was obtained for analysis after separated from the solid catalyst by filtration. Composition of the reaction product is shown in Table 8.

EXAMPLE 15

Pd-HBeta, Isomerization (250° C., 5 hr) Followed by Hydrogenation

Two grams of Pd-HBeta catalyst (no hydrogen reduction) and 20 grams of oleic acid were loaded into the reactor under nitrogen. After sealed, the reactor was purged three times with ultra high purity nitrogen. A nitrogen pressure of 50 psig was approached at room temperature after a leak test at 600 psig $N_2$ showed a good sealing. With an active stirring at 1000 RPM, the mixture of oleic acid and catalyst was heated up to 250° C. within 30 minutes and maintained for 5 h. Then the nitrogen was replaced with 500 psig hydrogen and reaction was continued for another 2 h. The mixture was brought out of the reactor and the product was obtained for analysis after separated from the solid catalyst by filtration. Composition of the reaction product was shown in Table 8.

It shows that metallic palladium with hydrogenation function existed on the catalyst, therefore, no prereduction with hydrogen is necessary. The conversion of $C_{18}$ unsaturated fatty acid was 95.63 wt % with a selectivity to branched fatty

TABLE 7

| Example | <=$C_{10}$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | lacton |
|---|---|---|---|---|---|---|---|---|---|---|---|---|---|
| 4 | 0.59 | 1.79 | 0.25 | 2.4 | 0 | 3.9 | 11 | 1.9 | 10.8 | 53.21 | 2.21 | 8.04 | 4.02 |

EXAMPLE 14

Pd-HBeta, Isomerization (280° C., 5 h) Followed by Hydrogenation acids of 67.83 wt %. There was no oligomerization or hydrocracked products.

TABLE 8

| Example | <=$C_{10}$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | lacton |
|---|---|---|---|---|---|---|---|---|---|---|---|---|---|
| 5 | 0.58 | 2.05 | 0 | 1.7 | 0 | 3.5 | 9 | 0 | 9.88 | 56.54 | 2.19 | 14.4 | 0.24 |
| 6 | 0 | 0.32 | 0.1 | 0.7 | 0 | 2.5 | 3.9 | 0 | 7.46 | 50.44 | 3.26 | 24.11 | 7.18 |

EXAMPLE 16

Pt-HY

Ion exchange was carried out on $NH_4^+$ Y zeolite (Si/Al=12) using tetraammineplatinum nitrate solution. The exchanged catalyst was calcined in air at 550° C. before use. Two grams of this catalyst (Pt-HY) and 20 grams of oleic acid were loaded into the reactor under nitrogen. After sealed, the reactor was purged three times with ultra high purity nitrogen. A nitrogen pressure of 50 psig was approached at room temperature after a leak test at 600 psig $N_2$ showed a good sealing. With stirring at 1000 RPM, the mixture of oleic acid and catalyst was heated up to 280° C. within 30 minutes and maintained for 5 h. After cooled down to 200° C., the nitrogen was replaced with 500 psig hydrogen and reaction was continued for another 3 h. After cooled down to room temperature within 20 minutes, the mixture was brought out of the reactor and the product was obtained for analysis after separated from the solid catalyst by filtration with slightly heating. Composition of the reaction product was shown in Table 9.

The conversion of $C_{18}$ unsaturated fatty acid was 89.63 wt % with a selectivity to branched fatty acids of 47.16 wt %.

EXAMPLE 17

Pt-HMor

Ion exchange was carried out on $NH_4^+$ Mordenite zeolite (Si/Al=20) using tetraammineplatinum nitrate solution. The exchanged catalyst was calcined in air at 550° C. before use. Two grams of this catalyst (Pt-HMor) and 20 grams of oleic acid were loaded into the reactor under nitrogen. After sealed, the reactor was purged three times with ultra high purity nitrogen. A nitrogen pressure of 200 psig was approached at room temperature after a leak test at 600 psig $N_2$ showed a good sealing. With stirring at 1000 RPM, the mixture of oleic acid and catalyst was heated up to 280° C. within 30 minutes and maintained for 5 h. After cooled down to 200° C., the nitrogen was replaced with 500 psig hydrogen and reaction was continued for another 4 h. After cooled down to room temperature within 20 minutes, the mixture was brought out of the reactor and the product was obtained for analysis after separated from the solid catalyst by filtration with slightly heating. Composition of the reaction product was shown in Table 9.

TABLE 9

| Example | <=$C_{10}$ | i-$C_{12}$ | $C_{12}$ | i-$C_{14}$ | $C_{14}^1$ | $C_{14}$ | i-$C_{16}$ | $C_{16}^1$ | $C_{16}$ | i-$C_{18}$ | $C_{18}^1$ | $C_{18}$ | lacton |
|---|---|---|---|---|---|---|---|---|---|---|---|---|---|
| 7 | 0 | 0 | 0 | 1.59 | 0 | 1.41 | 0.23 | 0 | 12.26 | 33.59 | 7.73 | 37.71 | 5.48 |
| 8 | 0.84 | 2.1 | 0.33 | 2.43 | 0 | 4.03 | 14.3 | 0.62 | 11.45 | 50.14 | 0.74 | 9.25 | 3.77 |

We claim:

1. A process for the isomerization of a feedstock which comprises unsaturated linear fatty acids, alkyl esters of unsaturated fatty acids or mixtures thereof, wherein said process comprises subjecting said feedstock to an isomerization reaction in the presence of an acidic catalyst having a three-dimensional channel pore structure wherein at least one channel structure has a pore size diameter of at least 6 Å wherein said acidic catalyst is not loaded with metal ions.

2. The process of claim 1, wherein the isomerization of said feedstock comprises branching of the fatty acids or alkyl esters thereof.

3. The process of claim 1 wherein said acidic catalyst comprises a zeolite, acidic clay, molecular sieve, or mixtures thereof.

4. The process of claim 3 wherein said acidic catalyst comprises a zeolite.

5. The process of claim 4 wherein said zeolite comprises at least one of the following framework structures: CON, DFO, FAU, AES, AFY, BEA, BPH, EMT, GME, or mixtures thereof.

6. The process of claim 4 wherein the $SiO_2/Al_2O_3$ ratio of the zeolite is at least 2.

7. The process of claim 4 wherein said zeolite contains at least one channel structure having a pore diameter of at least 6.5 Å.

8. The process of claim 4 wherein said zeolite contains at least one channel structure having a pore diameter of at least 7 Å.

9. The process according to claim 1 wherein the feedstock comprises of at least 50% by weight of unsaturated fatty acids, alkyl esters of unsaturated fatty acids or mixtures thereof.

10. The process of claim 9 wherein the feedstock comprises of at least 70% by weight oleic acid.

11. The process claim 10 wherein at least part of the isomerization is performed at a temperature of between 100° C. and 350° C.

12. The process of claim 11 wherein at least part of the isomerization is carried out at a temperature of between 230° C. and 285° C.

13. The process of claim 1 wherein said isomerization is conducted in a batch reactor.

14. The process of claim 1 wherein said isomerization is conducted in a fixed bed continuous flow reactor.

15. The process of claim 13 wherein the feedstock is contacted with the catalyst for a period of at least 30 minutes.

16. The process of claim 13 wherein the amount of catalyst used is between 0.5 and 20% by weight of the feedstock in the batch reactor.

17. The process of claim 13 wherein the weight hour space velocity is between 0.1 and 25 in a continuous flow reactor.

18. The process of claim 4 wherein said zeolite having a three-dimensional pore structure comprises at least one pore structure containing 10-membered rings as catalysts.

19. The process of claim 4 wherein said zeolite having a three-dimensional pore structure comprises at least one pore structure containing 12-membered rings as catalysts.

20. The process of claim 4 wherein said zeolite having a three-dimensional pore structure comprises at least one pore structure containing at least one ring having greater than 12 members as catalysts.

21. A process for the isomerization of a feedstock which comprises unsaturated linear fatty acids, alkyl esters of unsaturated fatty acids or mixtures thereof, wherein said process comprises subjecting said feedstock to an isomerization reaction in the presence of an acidic zeolite catalyst having a three-dimensional channel structure wherein at least one channel structure comprises rings having at least 12 members as catalysts, wherein said acidic catalyst is not loaded with metal ions.

22. The process of claim 6 wherein the $SiO_2/Al_2O_3$ ratio of the zeolite is at least 10.

* * * * *